United States Patent [19]
Palfreyman et al.

[11] 4,421,767
[45] Dec. 20, 1983

[54] COMPOUNDS AND METHODS FOR TREATING DEPRESSION

[75] Inventors: Michael G. Palfreyman, Fegersheim; Ian A. McDonald, Truchtersheim, both of France

[73] Assignee: Merrell Toraude et Compagnie, Strasbourg, France

[21] Appl. No.: 417,751

[22] Filed: Sep. 13, 1982

Related U.S. Application Data

[63] Continuation-in-part of Ser. No. 268,553, Jun. 1, 1981, abandoned.

[51] Int. Cl.³ .................. C07C 101/77; C07C 101/72; A61K 30/95; A61K 31/24
[52] U.S. Cl. .................................. 424/319; 424/309; 560/40; 562/445; 562/446
[58] Field of Search ................. 424/309, 319; 560/40; 562/445, 446

[56] References Cited

U.S. PATENT DOCUMENTS

| | | | |
|---|---|---|---|
| 3,023,235 | 2/1962 | Leonard | 560/40 |
| 3,046,300 | 7/1962 | Sletzinger et al. | 560/40 |
| 3,329,711 | 7/1967 | Hegedus et al. | 560/40 |
| 3,553,258 | 1/1971 | Kaiser et al. | 560/40 |
| 3,725,470 | 5/1968 | Brelschneider | 564/165 |

FOREIGN PATENT DOCUMENTS

| | | | |
|---|---|---|---|
| 34 | 12/1978 | European Pat. Off. | 562/444 |
| 7600 | 2/1980 | European Pat. Off. | 562/444 |
| 7815567 | 12/1978 | France | 562/444 |
| 998355 | 7/1965 | United Kingdom | 562/444 |

OTHER PUBLICATIONS

Chari et al., Tet. Letters, #2, pp. 111–114 (1979).
Chari, Univ. Microfilms Intntl. (1980).

*Primary Examiner*—James H. Reamer
*Attorney, Agent, or Firm*—William J. Stein; Gary D. Street; Raymond A. McDonald

[57] ABSTRACT

Compounds of the formula:

$$R-\underset{NH}{\underset{|}{C}}(=CH_2)-CH-CO_2H \quad (I)$$

$$R_1-\underset{NH}{\underset{|}{C}}(=CHX)-CH-CO_2H \quad (II)$$

or $$R_1-\underset{NH_2}{\underset{|}{C}}(=CX_2)-CH-CO_2H \quad (III)$$

wherein:
X is fluorine, chlorine, or bromine;
R is the group $R_2$ as defined below;
$R_1$ is a group of the formula:

[structures shown: phenol derivatives]

or the group $R_2$ as defined below; wherein $R_2$ is:

[various dihydroxy/hydroxy phenyl structures with $R_3$ and $R_4$ substituents]

wherein $R_3$ is hydrogen, $(C_1-C_4)$alkyl, or $(C_1-C_4)$alkoxy, and
$R_4$ is $(C_1-C_4)$alkyl or $(C_1-C_4)$alkoxy;
or a $(C_1-C_8)$alkyl ester thereof; or a non-toxic pharmaceutically acceptable salt thereof, inhibit MAO in vivo and can be administered either alone or in combination with an aromatic L-amino acid decarboxylase inhibitor for the treatment of depression.

36 Claims, No Drawings

COMPOUNDS AND METHODS FOR TREATING DEPRESSION

This application is a continuation-in-part of copending application Ser. No. 268,553 filed June 1, 1981, now abandoned.

This invention relates to pharmacologically-active novel compounds, to methods of preparation of the compounds, and to pharmaceutical compositions containing the compounds.

The class of compounds known as monoamine oxidase inhibitors (MAO inhibitors) has been employed in psychiatry for over 20 years for the treatment of depression [See Goodman and Gilman, *The Pharamacological Basis of Therapeutics*, 6th Ed., McMillan Publishing Co., Inc., N.Y., 1980, pages 427–430]. MAO Inhibitors currently used in the U.S.A. for treating depression are tranylcypromine (PARNATE, SKF), phenelzine (NARDIL, Parke-Davis), and isocarboxazid (MARPLAN, Roche). In addition, another MAO inhibitor, pargyline (EUTRON, Abbott), is available for the treatment of hypertension [See *Physicians' Desk Reference*, 34th Ed., Medical Economics Co., Oradell, N.J., 1980, pages 1327–1328 (phenelzine), pages 1466–1468 (isocarboxazid), pages 1628–1630 (tranylcypromine), and pages 521–522 (pargyline)]. MAO Inhibitors can also be employed to treat other psychiatric disorders, such as phobic anxiety states.

It is believed that the MAO inhibitors act to alleviate psychiatric disorders, such as depression, by increasing the concentration of one or more biogenic monoamines in the central nervous system. The monoamine oxidase enzyme (MAO) plays an important role in the metabolic regulation of the monoamines since it catalyzes the biodegradation of the monoamines through oxidative deamination. By inhibiting MAO, the degradation of the monoamines is blocked and the result is an increase in the availability of the monoamines for their physiological functions. Among the physiologically active monoamines which are known substrates for MAO are: (a) so-called "neurotransmitter" monoamines, such as the catecholamines (e.g. dopamine, epinephrine, and norepinephrine) and the indoleamines (e.g. tryptamine and 5-hydroxytryptamine), (b) the so-called "trace" amines (e.g. o-tyramine, phenethylamine, tele-N-methylhistamine), and (c) tyramine.

The usefulness of the MAO inhibitors in treating depression has been limited because the administration of such agents can potentiate the pharmacological actions of certain food substances or drugs leading to dangerous and sometimes lethal effects. For example, persons receiving a MAO inhibitor must avoid the ingestion of foods which have a high tyramine content (such as cheese) because the MAO inhibitor will block the metabolic degradation of tyramine in the gut and liver resulting in high circulating levels of tyramine, consequent release of catecholamines in the periphery, and finally serious hypertension. The potentiation by a MAO inhibitor of the pressor effect of tyramine arising from the ingestion of cheese, and the hypertensive episode produced thereby, are commonly known as the "cheese reaction" or "cheese effect". Moreover, persons on conventional MAO therapy can not be given directly-acting sympathomimetic drugs (or precursors thereof) which are themselves substrates for MAO (e.g. dopamine, epinephrine, norepinephrine, or L-dopa) and of indirectly-acting sympathomimetic drugs (e.g. amphetamines or over-the-counter cold, hay-fever, or weight control preparations which contain a vasoconstrictor). The potentiation of the pressor effects of indirectly-acting sympathomimetic drugs is especially profound. This is because such drugs act peripherally primarily by releasing catecholamines in nerve endings, and the concentration of the liberated cathecholamines will be dangerously elevated if the matabolic degradation of the catecholamines via MAO is blocked. In addition, a particular MAO inhibitor should not be used in combination with another MAO inhibitor or with hypotensive agents, dibenzapine antidepressants, meperidine, CNS depressants, and anticholinergic agents.

Biochemical and pharmacological studies indicate that the MAO enzyme exists in two forms known as "MAO Type A" (MAO-A) and "MAO Type B" (MAO-B). The forms differ in their distribution in body organs, in their substrate specificity, and in their sensitivity to inhibitors. In general, MAO-A selectively oxidizes the so-called "neurotransmitter" monoamines (epinephrine, norepinephrine, and 5-hydroxytryptamine) while MAO-B selectively oxidizes the "trace" monoamines (o-tyramine, phenethylamine, and tele-N-methylhistamine). Both MAO-A and MAO-B oxidize tyramine, tryptamine, and dopamine. However, in man, dopamine has been shown to be a preferred substrate for MAO-B. The forms also differ in their sensitivity to inhibition, and thus, can be preferentially inhibited depending upon the chemical structure of the inhibitor and/or the relative concentrations of the inhibitor and the enzyme. The MAO inhibitors currently sold in the U.S.A. for the therapy of depression (tranylcypromine, phenelzine, and isocarboxazid) are not preferential in their action upon MAO. However, various chemical compounds are known in the art to be preferential inhibitors of MAO, the most important being clorgyline, pargyline, and L-deprenyl which are all reported to be clinically effective antidepressant agents. MAO-A is preferentially inhibited by clorgyline, while MAO-B is preferentially inhibited by pargyline and L-deprenyl. It should be observed that the "selectivity" of a MAO inhibitor arises because the inhibitor has a greater affinity for one form of the enzyme. Thus, the selectivity of a MAO inhibitor for MAO-A or MAO-B in vivo will be dose-dependent, selectivity being lost as the dosage is increased. Clorgyline, pargyline, and L-deprenyl are selective inhibitors at lower dosages, but are not selective inhibitors at higher dosages. The literature concerning MAO-A and MAO-B and the selective inhibition thereof is extensive [See, for example, Goodman and Gilman, ibid, pages 204–205; Neff et al, *Life Sciences*, 14, 2061 (1974); Murphy, *Biochemical Pharmacology*, 27, 1889 (1978); Knoll, Chapter 10, pages 151–171 and Sandler, Chapter 11, pages 173–181, in *Enzyme Inhibitors as Drugs*, M. Sandler Ed., McMillan Press Ltd., London, 1980; Lipper et al., *Psychopharmacology*, 62, 123 (1979); Mann et al., *Life Sciences*, 26, 877 (1980); and various articles in *Monoamines Oxidase: Structure, Function, and Altered Functions*, T. Singer et al. Ed., Academic Press, N.Y., 1979].

Of the selective inhibitors of MAO, L-deprenyl is of interest since the "cheese effect" is not observed at the low dosages where preferential inhibitions of MAO-B occur [See Knoll, TINS, pages 111–113, May 1979]. This observation is not unexpected since the intestinal mucosa contains predominantly MAO-A which, because it is not inhibited, permits oxidation and removal of the ingested tyramine. The selectivity of L-deprenyl for MAO-B may account for its ability to potentiate L-dopa for the treatment of Parkinson's disease without producing peripheral side effects, such as hypertension due to potentiation of pressor catecholamines [See Lees et al., *Lancet*, pages 791–795, Oct. 15, 1977 and Birkmeyer, *Lancet*, pages 439–443, Feb. 26, 1977].

In a compound aspect, the invention comprehends chemical compounds of the formula:

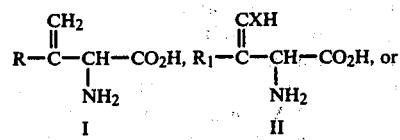

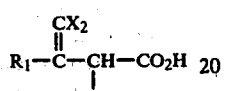

wherein:
X is fluorine, chlorine, or bromine;
R is the group $R_2$ as defined below;
$R_1$ is a group of the formula:

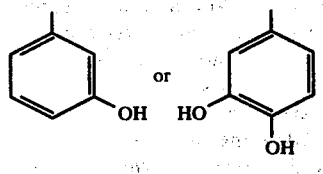

or the group $R_2$ as defined below;
wherein $R_2$ is:

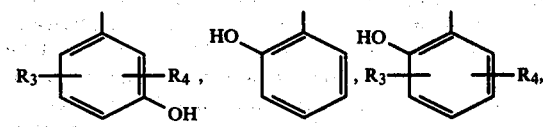

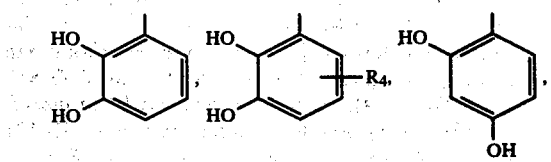

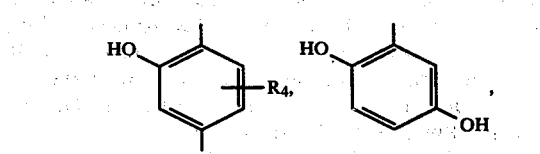

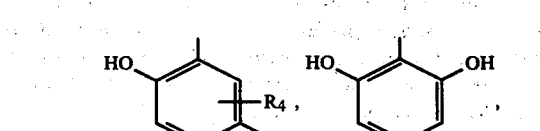

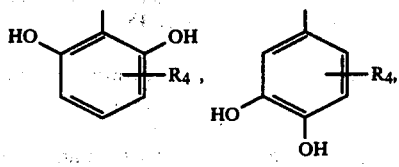

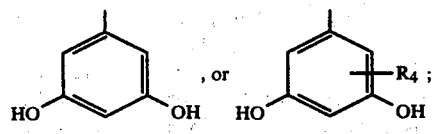

wherein $R_3$ is hydrogen, $(C_1-C_4)$alkyl, or $(C_1-C_4)$alkoxy, and $R_4$ is $(C_1-C_4)$alkyl or $(C_1-C_4)$alkoxy; or a $(C_1-C_8)$alkyl ester thereof; or a non-toxic pharmaceutically acceptable salt thereof.

The term "$(C_1-C_4)$alkyl" contemplates the methyl, ethyl, propyl, iso-propyl, n-butyl, tert-butyl, and iso-butyl groups. Methyl is preferred. The term "$(C_1-C_4)$alkoxy" contemplates the methoxy, ethoxy, n-propoxy, iso-propoxy, iso-butoxy, tert-butoxy, and n-butoxy groups. Methoxy is preferred. The $(C_1-C_8)$alkyl esters of the compounds of Formula I, II, or III are those wherein the alkyl group forming the ester with the carboxyl group is either straight or branched and contains from 1 to 8 carbons. Examples of esters are methyl, ethyl, propyl, iso-propyl, n-butyl, iso-butyl, tert-butyl, n-hexyl, n-heptyl, or n-octyl. The methyl and ethyl esters are preferred. The ester function must be chosen so that it is capable of being removed to form the free acid in vivo.

It will be understood that when $R_2$ is a phenyl group containing one or two —OH groups in combination with other substituents, such as the following phenyl groups:

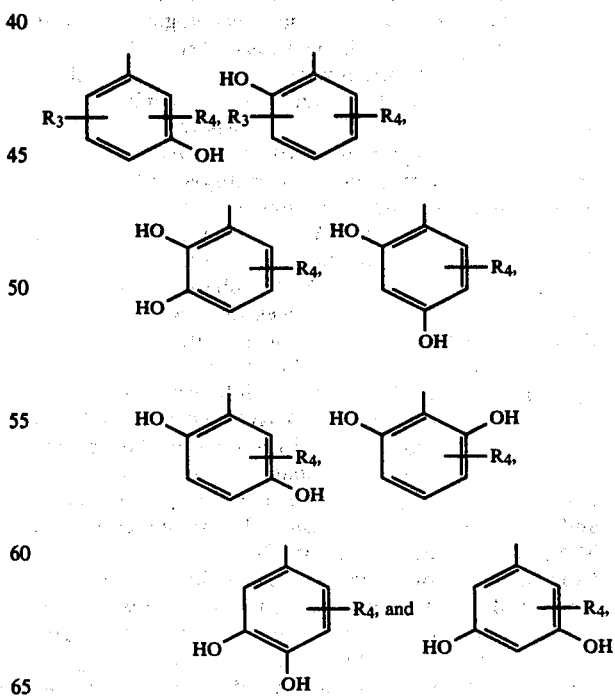

the substituents (represented by $R_3$ or $R_4$) may be located at any of the available positions of the phenyl ring. Illustrative examples of such substituted phenyl groups are:

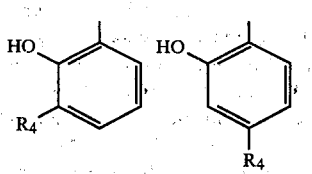,

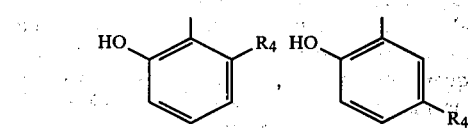,

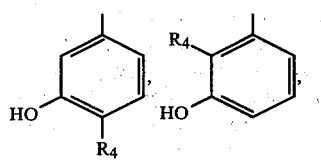,

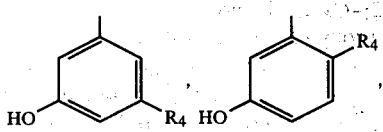,

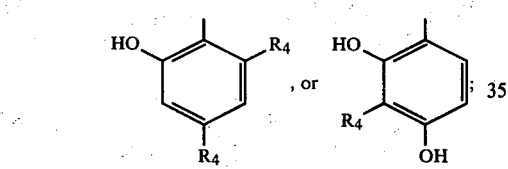, or wherein R$_4$ is (C$_1$-C$_4$)alkyl, (C$_1$-C$_4$)alkoxy, or fluorine. Preferably R$_4$ is methyl, ethyl, methoxy, or ethoxy. Methyl is most preferred.

Suitable non-toxic pharmaceutically acceptable salts of the compounds of Formula I, II, or III are known in the art and include acid addition salts formed by protonation of the α-amino group and salts formed by neutralization of the carboxylic acid function. As with any amino acid, the compounds may exist in the form of a zwitterion. Examples of acid addition salts are those formed from the following acids: hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic, and benzenesulfonic. Examples of salts formed by neutralization of the carboxylic acid are metallic salts (e.g. sodium, potassium, lithium, calcium, or magnesium) and ammonium or (substituted) ammonium salts. The potassium and sodium salts are preferred.

Preferred classes of compounds are:
(i) compounds of Formula II or III wherein R$_1$ is 3-hydroxyphenyl.
(ii) compounds of Formula I, II, or III wherein R$_1$ is

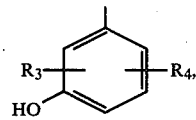

wherein R$_3$ is hydrogen, (C$_1$-C$_4$)alkyl, or (C$_1$-C$_4$)alkoxy and R$_4$ is (C$_1$-C$_4$)alkyl or (C$_1$-C$_4$)alkoxy.
(iii) compounds as defined in (ii) wherein R$_3$ is hydrogen.
(iv) compounds as defined in Formula I, II, or III wherein X is fluorine.
(v) compounds as defined in (i), (ii), and (iii) wherein X is fluorine.

Preferred embodiments of the compounds of the invention are:
2-amino-4-fluoro-3-(2'-hydroxyphenyl)-3-butenoic acid,
2-amino-4-fluoro-3-(3'-hydroxyphenyl)-3-butenoic acid,
2-amino-4-fluoro-3-(2',3'-dihydroxyphenyl)-3-butenoic acid,
2-amino-4-fluoro-3-(2',4'-dihydroxyphenyl)-3-butenoic acid,
2-amino-4-fluoro-3-(2',5'-dihydroxyphenyl)-3-butenoic acid,
2-amino-4-fluoro-3-(2',6'-dihydroxyphenyl)-3-butenoic acid,
2-amino-4-fluoro-3-(3',4'-dihydroxyphenyl)-3-butenoic acid,
2-amino-4-fluoro-3-(3',5'-dihydroxyphenyl)-3-butenoic acid,
2-amino-4-fluoro-3-(3'-hydroxy-4'-methylphenyl)-3-butenoic acid.

The compounds of Formula I, II, or III are in vivo precursors (or "prodrugs") of certain substances which are irreversible inhibitors of MAO, and said compounds are useful in psychiatry for the treatment of depression. The compounds of Formula I, II, or III are not irreversible inhibitors of MAO in vitro. In order to produce irreversible inhibition of MAO in vivo and to exert their antidepressant effect, the compounds of Formula I, II, or III must be transformed into active metabolites which are the 2-phenylallylamine compounds shown below respectively in Formula IV, V, or VI:

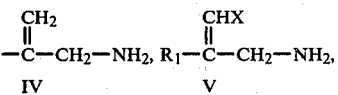

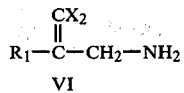

wherein X, R, and R$_1$ have the meanings defined supra.

The in vivo transformation of the compounds of Formula I, II, or III to the active metabolites of Formula IV, V, or VI occurs through a decarboxylation reaction catalyzed by an enzyme known as "aromatic-L-amino acid decarboxylase" (AADC). AADC is known to decarboxylate various biologically important amino acids (such as dopa, tyrosine, phenylalanine, tryptophan, and 5-hydroxytryptophan) to form the corresponding monoamines. When a compound of Formula I, II, or III is in the form of a (C$_1$-C$_8$)alkyl ester, such compound is not a substrate for AADC. Hence, before decarboxylation can take place, the ester function is hydrolyzed in vivo, either enzymatically or non-enzymatically, to provide a compound of Formula I, II, or III, which contains a free carboxylic acid function. Moreover, in order to be a substrate for AADC, a compound of Formula I, II, or III must be in the form of the enantiomer corresponding to that of a natural- or L-amino acid.

The antidepressant compounds of Formula IV, V, or VI which inhibit MAO in vitro and in vivo are described and claimed in the pending U.S. application of P. Bey entitled "Allylamine MAO Inhibitors", Ser. No. 268,555 filed June 1, 1981.

Because AADC exists in the brain and in extracerebral tissues, the decarboxylation of a compound of Formula I, II, or III to form the corresponding metabolite of Formula IV, V, or VI will occur both cerebrally and extracerebrally. However, the metabolites of Formula IV, V, or VI formed extracerebrally penetrate poorly into the brain, and are not readily available for inhibition of brain MAO. The occurrence of extracerebral decarboxylation, therefore, will decrease the amount of the administered compound available extracerebrally for penetration into the brain and subsequent decarboxylation by brain AADC. The amount of compound available extracerebrally for brain penetration can be increased, however, by administering the compound of Formula I, II, or III in combination with a compound capable of preferentially inhibiting extracerebral AADC. Thus, when administered in combination with an extracerebral AADC inhibitor, the compounds of Formula I, II, or III will provide a "site-directed" or "site-selective" inhibition of MAO, such inhibition occurring preferentially in the brain rather than in extracerebral tissues.

As compared to the administration of a compound of Formula I, II, or III alone, the administration of a compound of formula I, II, or III in combination with an extracerebral AADC inhibitor can achieve a pharmacologically meaningful beneficial effect on brain MAO activity using less administered compound. Moreover, this effect can be obtained with proportionally less propensity for producing the "cheese effect" or other peripheral complications associated with extracerebral MAO inhibition.

Suitable AADC inhibitors for use in combination with the compounds of Formula I, II, or III will be apparent to those skilled in the art. Both competitive and irreversible inhibitors can be used. At the dosages used, the AADC inhibitor must be capable of substantially inhibiting AADC extracerebrally without substantially inhibiting AADC in the brain. Examples of AADC inhibitors for use in combination with a compound of Formula I, II, or III are carbidopa and benzerazide, compounds which also have been found useful for blocking the peripheral decarboxylation of exogenous L-dopa administered for the treatment of Parkinsonism [See Chapter 21, especially pages 482–483, "The Pharmacological Basis of Therapeutics", Goodman and Gilman Ed., McMillan Publishing Co., Inc., N.Y., 6th Ed., 1980]. Other examples of suitable AADC inhibitors are the 2-amino-2-(monofluoromethyl or difluoromethyl)-3-(monohydroxy-phenyl or dihydroxyphenyl)-propionic acids and like compounds, which are described in Belgian Pat. Nos. 868,881 and 882,105. Preferred compounds are 2-amino-2-(monofluoromethyl or difluoromethyl)-3-(3',4'-dihydroxyphenyl)propionic acid, and the 2',3'- or 2',5'-dihydroxyphenyl isomers thereof.

The preparation of 2-amino-3-phenyl-3-butenoic acid and 2-amino-3-(3'-hydroxyphenyl)-3-butenoic acid from methyl 3-phenyl-2-butenoate and methyl 3-(3'-tetrahydropyranyloxyphenyl)-2-butenoate, respectively, is described by R. Chari in the Doctoral Dissertation entitled "Synthesis of $\beta,\gamma$-Unsaturated Amino Acids as Potential Irreversible Enzyme Inhibitors" University of Detroit, 1979 (available in print from University Microfilm International, Ann Arbor, Mich.). The compounds of Formula I in general can be prepared according to the method of Chari, or a modification thereof, depending upon the type of substitution in the phenyl ring and the consequent sensitivity of the double bond to acid. The starting materials for the preparation of the compounds of Formula I are the alkyl 2-butenoate compounds of Formula VII:

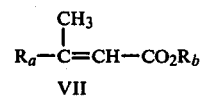

VII wherein:
$R_b$ is $(C_1-C_4)$alkyl, and
$R_a$ is a group of the formula:

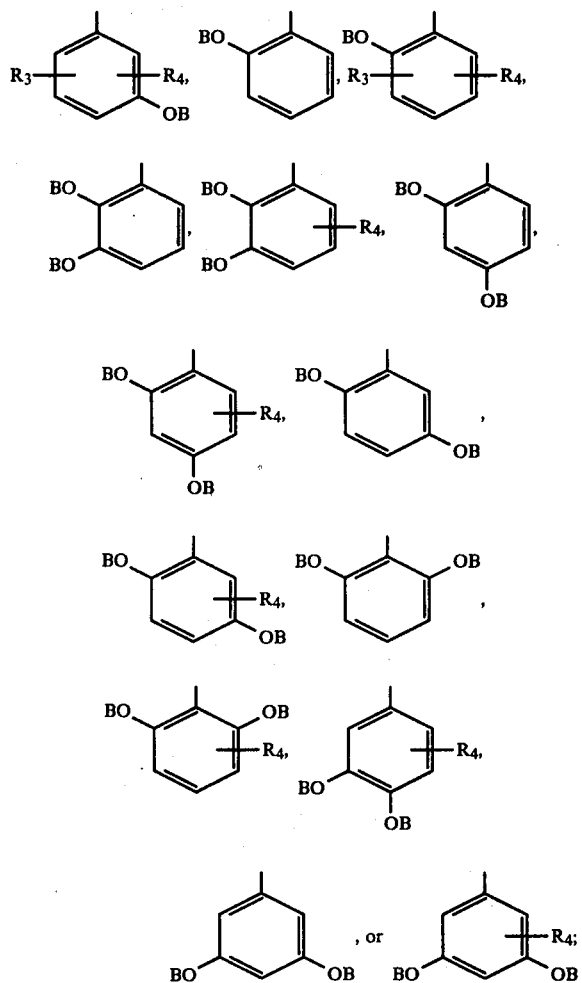

wherein:

$R_3$ and $R_4$ have the meanings defined supra and

B is a protecting group for an aromatic —OH group.

The preferred starting materials of Formula VII are those wherein $R_b$ is methyl, ethyl, or tert-butyl. The purpose of the group defined by $R_b$ is to protect the carboxy group from unwanted side reactions during subsequent process steps. The group represented by B in the definition of $R_a$ can be any group known to be useful in the art of chemistry for protecting an aromatic —OH group, which group is readily removable under conditions which will not cause side reactions (such as polymerization) involving the double bond. Suitable protecting groups are: tetrahydropyranyl, methoxymethyl, methoxyethoxy-methyl, tert-butyl, benzyl, or triphenylmethyl. Preferred protecting groups are those that can be removed under very mild conditions. The selection and utilization of a particular aromatic —OH protecting group are known per se in the art.

In the method of Chari, a compound of Formula VII is brominated in carbon tetrachloride at $-10°$ C. to form the corresponding alkyl dibromobutyrate compound of Formula VIII:

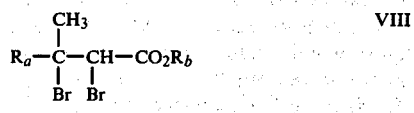

which upon treatment with ammonia in dimethyl sulfoxide (DMSO) affords an alkyl 2-amino-3-butenoate compound of Formula IX:

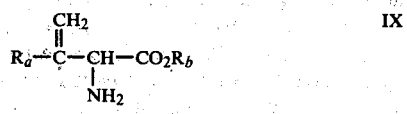

When the intermediate of Formula IX does not have a protected —OH group or an alkoxy group in the 2- and/or 4-position of the phenyl ring, the intermediate can be converted to a compound of Formula I in two stages: (a) treatment with an acid (preferably dilute hydrochloride acid or saturated ethereal hydrogen chloride) under mild conditions (a temperature of 0° to 25° C.) for up to 16 days under which conditions the aromatic —OH protecting group (B) is removed, and (b) treatment with a strong acid (6 N hydrochloric acid) at reflux temperature under which conditions the ester group is hydrolyzed.

When the intermediate of Formula IX has a protected aromatic —OH group or an alkoxy group in the 2- and/or 4-position of the phenyl ring, the intermediate can be converted to a compound of Formula I by a three-stage process which comprises:

(a) alkaline hydrolysis (preferably with lithium hydroxide in dioxane/water) at ambient temperature to remove the ester alkyl group ($R_b$), (b) neutralization of the salt thus formed (to pH ca 4.0, preferably with dilute hydrochloric acid) to afford the corresponding free acid, and (c) treatment with an acid (preferably dilute hydrochloric acid or ethereal hydrogen chloride) under mild conditions (a temperature of 0° to 25° C.) for up to 16 hours to remove the aromatic —OH protecting group (B).

When $R_b$ in Formula IX is tert-butyl, steps (a) and (b) can be omitted. With acid sensitive intermediates, the three step process is preferred because the use of basic conditions and/or mild acid conditions to hydrolyze the ester function and to remove the protecting groups will minimize the occurence of side reactions involving the double bond (e.g. polymerization) which reactions are promoted under vigorous acidic conditions.

A modification of the above-described method involves the intermediate preparation and isolation of an N-protected 2-amino-3-butenoate compound of Formula X:

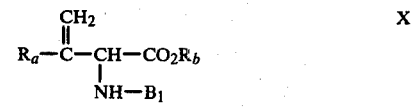

wherein:

$R_a$ and $R_b$ have the meanings defined supra, and $B_1$ is a protecting group for a primary α-amino group.

The group represented by $B_1$ can be any group known in the art to be useful for protecting a primary α-amino group, which group is readily removable under acidic conditions which will not cause side reactions (such as polymerization) involving the double bond. The selection of a particular protecting group and its method of utilization are known in the art. Examples of suitable protecting groups for the α-amino group are: formyl, acetyl, trifluoroacetyl, phthalyl, tosyl, benzenesulfonyl, benzyloxycarbonyl, (substituted)-benzyloxycarbonyl, (e.g. the p-chloro, p-bromo, p-nitro, p-methoxy, o-chloro, 2,4-dichloro, and 2,6-dichloro derivatives), t-butyloxycarbonyl (Boc), t-amyloxycarbonyl, isopropyloxycarbonyl, 2-(p-biphenyl)isopropyloxycarbonyl, allyloxycarbonyl, cyclopentyloxycarbonyl, cyclohexyloxycarbonyl, adamentyloxycarbonyl, phenylthiocarbonyl, or triphenylmethyl. The preferred α-amino protecting group is t-butyloxycarbonyl (Boc) which can be introduced by reaction with di-tert-butyl dicarbonate.

The intermediate for Formula X can be prepared by treating a compound of Formula IX, as prepared according to the above-described method of Chari, with di-tert-butyl dicarbonate in tetrahydrofuran at 60° C. for about 2-4 hours. The intermediate of Formula X, regardless of the type of substitution in the phenyl ring can be converted to a compound of Formula I by a three-stage procedure which comprises:

(a) alkaline hydrolysis (preferably with lithium hydroxide in dioxane/water) at ambient temperature to remove the ester alkyl group ($R_b$), (b) neutralization of the salt thus formed (to pH ca 4.0, preferably with dilute hydrochloric acid) to afford the corresponding free acid, and (c) treatment with an acid (preferably dilute hydrochloric acid or ethereal hydrogen chloride) under mild conditions (a temperature of 0° to 25° C.) for up to 16 hours to remove the aromatic —OH protecting group (B) and the α-amino group ($B_1$). When $R_b$ in Formula X is tert-butyl, steps (a) and (b) can be omitted.

The modified method, as described above, is especially preferred for making the compounds of Formula I which have the —OH group or an alkoxy group at the 2-position or 4-position of the phenyl ring. Use of the N-protected derivative of Formula X in the modified procedure rather than the free amine intermediate of Formula IX, avoids decomposition of the amino acid during the subsequent base hydrolysis step and aids in purification of the hydrolysis product.

The compounds of Formula II can be prepared in manner known per se by the method depicted below:

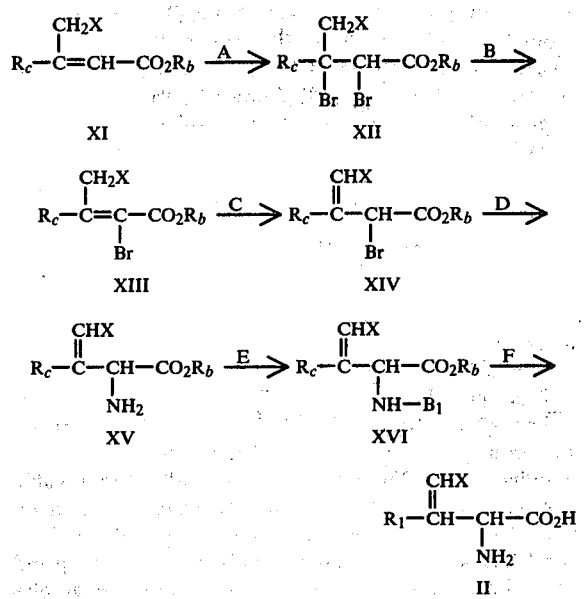

In the above reaction scheme, $R_c$ is a group of the formula:

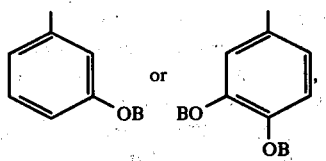

or a group as defined by $R_a$ in Formula VII; $R_b$ is $(C_1-C_4)$alkyl; $B_1$ is a protecting group for a primary α-amino group; and X is fluorine, chlorine, or bromine except that the protecting group (B), as defined by $R_c$ or $R_a$, cannot be tetrahydropyranyl. In Step A, an alkyl 4-halo-2-butenoate compound of Formula XI is brominated in manner known per se, preferably in carbon tetrachloride at 0° C., to afford an alkyl 2,3-dibromo-4-halobutenoate compound of Formula XII. In Step B, the compound of Formula XII is dehydrohalogenated in manner known per se, preferably by treatment with sodium hydride in tetrahydrofuran (THF) at reflux temperature, to give the alkyl 4-halo-2-bromo-2-butenoate compound of Formula XIII, which is then isomerized (Step C) in manner known per se to the corresponding 3-butenoate compound of Formula XIV, preferably by treatment with lithium diisopropylamide in THF at −78° C. In Step D, the 3-butenoate compound of Formula XIV is treated with ammonia, preferably in dimethylsulfoxide (DMSO), at ambient temperature to afford the alkyl 4-halo-2-amino-3-butenoate compound of Formula XV, which in Step E is treated in manner known per se to form the N-protected derivative of Formula XVI. The conversion (Step F) of the N-protected derivative of Formula XVI to a final product of Formula II can be accomplished by a three-stage procedure which comprises:

(a) alkaline hydrolysis (preferably with lithium hydroxide in dioxane/water) at ambient temperature to remove the ester alkyl group ($R_b$), (b) neutralization of the salt thus formed (to pH ca 4.0, preferably with dilute hydrochloric acid) to afford the corresponding free acid, and (c) treatment with an acid (preferably dilute hydrochloric acid or ethereal hydrogen chloride) under mild conditions (a temperature of 0° to 25° C.) for up to 16 hours to remove the aromatic —OH protecting group (B) and the α-amino protecting group ($B_1$). When $R_b$ in Formula XVI is tert-butyl, steps (a) and (b) can be omitted.

When it is desired to prepare a compound of Formula II in which the —OH group is present at the 3-position of the phenyl ring, and a —OH or alkoxy is not present in the 2- or 4-position of the phenyl ring, a further modified procedure can be used. This procedure is similar to that described above for preparing the compounds of Formula II, except that the starting material is a compound of Formula XI in which the aromatic —OH protecting group (B), as defined by $R_a$ can also be a $(C_1-C_4)$straight chain alkyl group. The preparation is carried out in a manner similar to that described above for Steps A, B, C, D, and E. However, the N-protected derivative formed in Step E can be converted to a compound of Formula II in one step by treatment with 47% hydrobromic acid at reflux temperature. Such treatment will remove the aromatic —OH protecting group (B), remove the ester alkyl function ($R_b$), and remove the α-amino protecting group ($B_1$). Alternatively the N-protected derivative can be treated with dilute hydrochloric acid or saturated ethereal hydrogen chloride to remove the α-amino protecting group before treatment with 47% hydrogen bromide.

In Step E, the preferred N-protecting group is tert-butoxycarbonyl (Boc) which can be introduced into a compound of Formula XV in manner known per se, such as by reaction with di-tert-butyl dicarbonate.

The compounds of Formula III can be prepared in a manner similar to that described for preparing the compounds of Formula II using as the starting material a compound of Formula XVII:

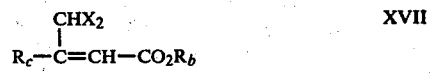

wherein $R_b$, $R_c$, and X have the meanings defined supra with respect to Formula XI.

The starting material of Formula VII, XI, or XVII can be prepared in known manner by the Wittig reaction by treating a ketone of the Formula:

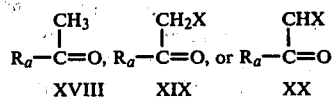

with a suitable trialkylphosphonoacetate in dimethoxyethane (DME) at 0° C. in the presence of sodium hydride. The ketones of Formula XVIII, XIX, or XX are either known compounds or they can be prepared from known compounds by methods known in the art or obvious modifications thereof. For example, the compounds of Formula XVIII can be halogenated in known manner to prepare the compounds of Formula XIX or XX or an appropriately substituted benzene compound can be acylated using a Friedel-Craft reaction.

It will be appreciated by those skilled in the art, that the compounds of Formula I, II, or III have an aromatic —OH group which can bear known substituents that are capable of being removed in vivo to generate the free aromatic —OH group. The derivatives of the compounds of Formula I, II, or III containing such substituents at the aromatic —OH group can be employed in place of the compounds of Formula I, II, or III for the treatment of depression, and such derivatives are equivalent to the compounds of Formula I, II, III for the purposes of this invention.

Since the compounds of Formula I, II, or III possess an asymetric carbon atom, enantiomers are possible, and the compounds of the invention may be in the form of the biologically active individual enantiomer or mixtures of the enantiomers, such as the racemate.

The compounds of Formula I, II, or III may be obtained in the form of a pure enantiomer either by resolving a desired racemic product or by resolving a racemic starting material or intermediate at any convenient stage of the synthesis. Methods of carrying out the resolution are well known in the art of chemistry. When dosage ranges are given herein, they are applicable to the racemate.

In addition, the compounds of Formula II can exist in forms wherein the substituents represented by X can be either cis or trans to the group represented by $R_1$. It is understood that the compounds of the invention may exist as the pure cis or trans form, or as mixtures thereof.

When employed to treat depression, the effective dosage of the compounds of Formula I, II, or III will vary according to the particular compound being employed, the severity and nature of the depression, and the particular subject being treated. In general, with the compounds of Formula I, effective results can be achieved by the oral or parenteral route at a dosage level of from about 20 to about 200 mg per day, while with the compounds of Formula II and III, effective results can be achieved by the oral or parenteral route at a dosage level of from about 0.01 to about 50 mg per day.

Therapy should be initiated at lower dosages, the dosage thereafter being increased until the desired effect is achieved.

When an AADC inhibitor is co-administered with a compound of Formula I, II, or III for the treatment of depression, the effective dosage of the AADC inhibitor must be capable of substantially blocking the AADC catalyzed decarboxylation of said compound extracerebrally without substantially blocking the AADC catalyzed decarboxylation in the brain. The effective dose will vary, however, according to the particular compound being employed and the dose of the antidepressant "prodrug" administered. In general, with carbidopa and benzerazide effective results can be achieved by the oral or parenteral route at a dosage level of about 50 to 500 mg per day, preferably about 50 to 250 mg. With the 2-halomethylated 2-amino-3-(substituted phenyl)-propionic acids described supra, effective results can be achieved by the oral or parenteral route at a dosage level of about 0.1 mg to 1000 mg per day. For example, with 2-amino-2-difluoromethyl-3-(3',4'-dihydroxyphenyl)propionic acid, and like compounds, the effective dose is about 10 to 1000 mg per day, preferably about 100 to 500 mg. With 2-amino-2-fluoromethyl-3-(3',4'-dihydroxyphenyl)-propionic acid, and like compounds, such as the 2,3-dihydroxyphenyl isomer thereof, the effective dose is about 0.1 to 50 mg per day, preferably about 0.5 to 10 mg.

It will be understood that the AADC inhibitor can be co-administered either substantially at the same time as or prior to the administration of a compound of Formula I, II, or III. When administered prior, the AADC inhibitor can be given up to 4 hours prior, depending upon the route of administration and severity of the conditions being treated.

When used in combination with an AADC inhibitor, a compound of Formula I, II, or III and the AADC inhibitor can be administered separately, each being contained in a formulation in which the compound or the AADC inhibitor is the sole active agent or they can be administered together in a formulation containing both the compound and the AADC inhibitor as active agents. When both agents are contained in a single formulation, the relative amounts of each agent can vary depending upon the particular compounds employed.

The compounds of this invention can be administered in various manners to achieve the desired effect. The compounds can be administered alone or in combination with pharmaceutically acceptable carriers or diluents, the proportion and nature of which are determined by the solubility and chemical properties of the compound selected, the chosen route of administration, and standard pharmaceutical practice. The compounds may be administered orally in solid dosage forms, e.g. capsules, tablets, powders, or in liquid forms, e.g. solutions or suspensions. The compound may also be injected parenterally in the form of sterile solutions or suspensions. Solid oral forms may contain conventional excipients, for instance: lactose, succrose, magnesium stearate, resins, and like materials. Liquid oral forms may contain various flavoring, coloring, preserving, stabilizing, solubilizing, or suspending agents. Parenteral preparations are sterile aqueous or nonaqueous solutions or suspensions which may contain various preserving, stabilizing, buffering, solubilizing, or suspending agents. If desired, additives, such as saline or glucose, may be added to make the solutions isotonic.

The amount of active compound administered will vary and can be any effective amount. Unit doses of these compounds can contain, for example, from about 10 μg to 100 mg of the compounds and may be administered, for example, one or more times daily, as needed.

The term "unit dosage form" is used herein to mean a single or multiple dose form containing a quantity of the active ingredient in admixture or otherwise in association with the diluent or carrier, said quantity being such that one or more predetermined units are normally required for a single therapeutic administration. In the case of multiple dose forms, such as liquids or scored tablets, said predetermined unit will be one fraction such as 5 ml (teaspoon) quantity of a liquid or a half or quarter of a scored tablet, of the multiple dose form.

In a composition aspect, the invention provides pharmaceutical compositions comprising a compound of the formula:

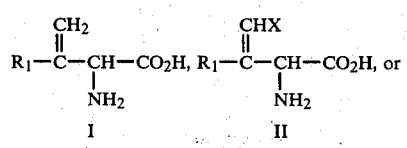

-continued

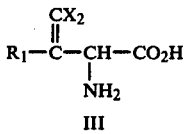

III wherein:
X is fluorine, chlorine, or bromine, and
R is the group $R_2$ as defined below;
$R_1$ is a group of the formula:

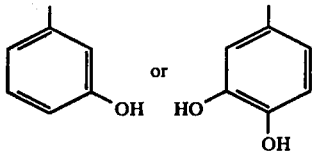

or the group $R_2$ as defined below; wherein $R_2$ is:

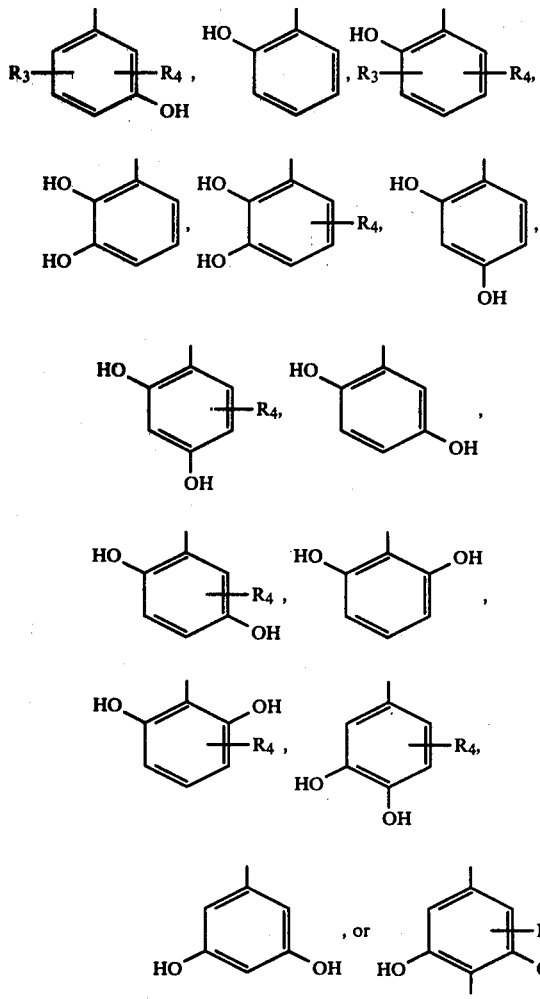

wherein $R_3$ is hydrogen, $(C_1-C_4)$alkyl, or $(C_1-C_4)$-alkoxy, and $R_4$ is $(C_1-C_4)$alkyl or $(C_1-C_4)$alkoxy; or a $(C_1-C_8)$alkyl ester thereof; or a non-toxic pharmaceutically acceptable salt thereof; and a pharmaceutically acceptable carrier or diluent thereof.

In another composition aspect, there is provided a pharmaceutical composition comprising (a) a compound of Formula I, II, or III, wherein X, R, $R_1$, $R_2$, $R_3$, and $R_4$ are as defined hereinabove, and (b) an aromatic-L-amino acid decarboxylase inhibitor. Preferably both active ingredients are in admixture with a pharmaceutically acceptable carrier or diluent therefor. Preferred aromatic-L-amino acid decarboxylase inhibitors are benzerazide, carbidopa, and a 2-amino-3-(monohydroxyphenyl or dihydroxyphenyl)propionic acid.

The pharmaceutical formulations are prepared in a manner well known per se in the pharmaceutical art. The carrier or diluent may be solid, semi-solid, or liquid material which serves as a vehicle, excipient, or medium for the active ingredient. Suitable diluents or carriers are well known per se. The pharmaceutical formulations may be adapted for enteral or parenteral use and may be administered to the patient in the form of tablets, capsules, suppositories, solutions, suspensions, or the like.

In the specific examples included herein-below, illustrative examples of suitable pharmaceutical formulations are described.

The following examples are illustrative of the processes of the invention. All temperature are in centrigrade.

EXAMPLE 1

α-Fluoro-3-methoxyacetophenone

A solution of 3-methoxyacetophenone (6.0 g) in acetic acid (20 ml) is treated slowly with bromine (6.4 g) so that the temperature does not rise above 20°. After the completion of the addition, the solution is stirred for 1 hour at 20°, and the acetic acid is completely evaporated. The residue is crystallized from ethanol to give α-bromo-3-methoxyacetophenone (7.51 g) as cream needles.

A mixture of α-bromo-3-methoxyacetophenone (6.87 g) and potassium hydrogen fluoride (7.0 g) in diethylene glycol (50 ml) is heated (100°) and stirred for 5 hours. The mixture is cooled, poured into ice/water, and extracted with ether. The ether extract is washed consecutively with saturated aqueous sodium bicarbonate and water, dried, and evaporated to yield a solid mass. This is recrystallized from a mixture of ethanol and ether to afford pure α-fluoro-3-methoxyacetophenone (3.28 g): colorless needles, m.p. 53°–54°:

NMR (CDCl$_3$): δ 3.82, s, 3H; 5.43, d (J=46 Hz), 2H; 6.93 to 7.53, m, 4H.

Analysis for $C_9H_9FO_2$: Found: C, 64.59; H, 5.34%: Requires: C, 64.28; H, 5.39%.

EXAMPLE 2

Ethyl 3-(3′-methoxyphenyl-4-fluoro-2-butenoate

A solution of diethyl ethoxycarbonylmethanephosphonate (5.6 g) in dimethoxyethane (80 ml) is added dropwise to a cooled (0°) suspension of sodium hydride (0.6 g) in dimethoxyethane (30 ml). The mixture is stirred at room temperature for 2 hours, and a solution of α-fluoro-3-methoxyacetophenone (4.20 g) in dimethoxyethane (100 ml) is added slowly. Stirring is continued for 30 minutes after the completion of the addition. The solution is cooled to about 10° and then poured into ice-water (200 ml) after which the mixture is extracted with ether. The ether solution is washed with water, dried, and evaporated to yield an orange oil (5.23 g). Purification is achieved by chromatography on silica gel (200 g) using light petroleum (90%)/ether (10%) as eluant whereupon there is obtained pure ethyl 3-(3′- methoxyphenyl)-4-fluoro-2-butenoate (3.92 g): almost colorless oil:

NMR (CDCl$_3$): δ 1.28, t (J=7 Hz), 3H; 3.77, s, 3H; 4.20, q (J=7 Hz), 5.83, d.d (J=47 Hz, 1.5 Hz); 6.15, s (broad), 1H; 6.73 to 7.43, m, 4H.

Analysis for C$_{13}$H$_{15}$FO$_3$: Found: C, 65.53; H, 6.44%; Requires: C, 65.53; H, 6.35%.

EXAMPLE 3

Ethyl 2,3-dibromo-3-(3'-methoxyphenyl)-4-fluorobutyrate

To a solution of ethyl 3-(3'-methoxyphenyl)-4-fluoro-2-butenoate (1.85 g) in carbon tetrachloride (40 ml) cooled to about −10° is added dropwise a solution of bromine (1.48 g) in carbon tetrachloride (10 ml). Stirring is continued at this temperature for 2 hours, after which the solution is evaporated to dryness. The residue is a pale orange oil (3.27 g) and is essentially pure ethyl 2,3-dibromo-3-(3'-methoxyphenyl)-4-fluorobutyrate:

NMR (CDCl$_3$): δ 1.23, t (J=7 Hz), 3H; 3.75, s, 3H; 4.20, q (J=7 Hz); 2H; 5.00, s, 1H; 5.35, d (J=50 Hz), 2H; 6.63 to 7.43, m, 4H.

EXAMPLE 4

Ethyl 2-bromo-3-(3'-methoxyphenyl)-4-fluoro-2-butenoate

A solution of ethyl 2,3-dibromo-3-(3'-methoxyphenyl)-4-fluorobutyrate (5.55 g) in tetrahydrofuran (10 ml) is added dropwise to a suspension of NaH (0.41 g) in tetrahydrofuran (40 ml). The mixture is refluxed for 5 hours, cooled, and carefully treated with water. The mixture is then extracted with ether. The ether extract is washed with water, dried, and evaporated to leave an orange oil (4.52 g). Purification is achieved by silica gel (200 g) chromatography using as eluant a mixture of light petroleum (90%)/ether (10%) whereupon there is obtained pure ethyl 2-bromo-3-(3'-methoxyphenyl)-4-fluoro-2-butenoate (3.85 g) almost colorless oil:

NMR (CDCl$_3$): δ 0.97, t (J=7 Hz), 3H; 3.78, s, 3H; 4.00, q (J=7 Hz), 2H; 5.35, d (J=48 Hz), 2H; 6.70 to 7.52, m, 4H.

Analysis for C$_{13}$H$_{14}$BrFO$_3$: Found: C, 49.18; H, 4.35%; Requires: C, 49.23; H, 4.45%.

EXAMPLE 5

Ethyl 2-bromo-3-(3'-methoxyphenyl)-4-fluoro-3-butenoate

A solution of ethyl 2-bromo-3-(3'-methoxyphenyl)-4-fluoro-2-butenoate (3.80 g) in tetrahydrofuran (15 ml) is added to a cooled (−75°) solution of lithium diisopropylamide prepared in the normal way from diisopropylamine (2.1 ml) and n-butyllithium (10 ml of a 1.5 M solution in hexane) in tetrahydrofuran (60 ml). After the addition, the reaction mixture is stirred for 90 minutes at −75°. Then 5% aqueous hydrochloric acid (10 ml), followed by water (20 ml), are added cautiously. The mixture is extracted with ether, and the ether extract is washed with dilute aqueous hydrochloric acid, then with water, dried, and evaporated to give 2-bromo-3-(3'-methoxyphenyl)-4-fluoro-3-butenoate (3.76 g) as a brown oil, and can be used without purification.

EXAMPLE 6

Ethyl 2-tert-butoxycarbonylamino-3-(3'-methoxyphenyl)-4-fluoro-3-butenoate

A cooled (5°) saturated solution of ammonia in dimethyl sulfoxide (15 ml) is added to ethyl 2-bromo-3-(3'-methoxyphenyl)-4-fluoro-3-butenoate (0.62 g) in a pressure vessel. The vessel is sealed and allowed to stand for 2 days at room temperature. The solution is then poured into ice-water and extracted with dichloromethane. The dichloromethane extract is washed thoroughly with water, dried, and evaporated to leave an orange oil (0.36 g). This substance is dissolved in tetrahydrofuran (30 ml) containing di-tert-butyl dicarbonate (0.31 g) and then stirred at 60° for 2 hours. Evaporation of the solvent and purification of the residue (0.64 g) by silica gel (10 g) chromatography using light petroleum (90%)/ether (10%) as eluant allows the isolation of pure racemic ethyl 2-tert-butoxycarbonylamino-3-(3'-methoxyphenyl)-4-fluoro-3-butenoate (0.22 g): colorless oil:

NMR (CDCl$_3$): δ 1.17, t (J=7 Hz), 3H; 1.42, s, 9H; 3.72, s, 3H; 4.13, q (J=7 Hz), 2H; 4.90, d (J=8 Hz), 1H; 5.30, d (broad, J+8 Hz), 1H; 6.85, d (J=82 Hz), 1H; 6.70 to 7.40, m, 4H.

Analysis for C$_{18}$H$_{24}$FNO$_5$: Found: C, 61.22, H, 6.66; N, 3.87%; Requires: C, 61.18; H, 6.85; N, 3.96%.

EXAMPLE 7

Ethyl 2-amino-3-(3'-methoxyphenyl)-4-fluoro-3-butenoate

A solution of ethyl 2-tert-butoxycarbonylamino-3-(3'methoxyphenyl)-4-fluoro-3-butenoate (218 mg) in ether (10 ml) saturated with dry HCl is left overnight by which time colorless needles crystallize. These are collected and dried to afford pure recemic ethyl 2-amino-3-(3'-methoxyphenyl)-4-fluoro-3-butenoate (150 mg): colorless needles, m.p. 141°-142°:

Analysis for C$_{13}$H$_{17}$ClFNO$_3$: Found: C, 54.22; H, 6.25; N, 4.67%; Requires: C, 53.89; H, 5.91; N, 4.83%.

EXAMPLE 8

2-Amino-3-(3'-hydroxyphenyl-4-fluoro-3-butenoic acid

A solution of ethyl 2-amino-3-(3'-methoxyphenyl)-4-fluoro-3-butenoate (150 mg) in 47% aqueous hydrobromic acid (10 ml) is refluxed for 3 hours after which the water is completely evaporated. The residue (orange oil, 112 mg) is dissolved in ethanol (1 ml) and treated with a slight excess of propylene oxide so that the pH is adjusted to about 4 to 5. The resulting precipitate is collected and subsequently recrystallized from ethanol/water whereupon pure racemic 2-amino-3-(3'-hydroxyphenyl)-4-fluoro-3-butenoic acid (29 mg) is obtained: colorless needles, m.p. 215°:

NMR (CD$_3$OD): δ 4.62, s, 1H; 6.28 to 7.13, m, 4H; 6.98, d (J=80 Hz), 1H.

Analysis for C$_{10}$H$_{10}$FNO$_3$: Found: C, 56.73; H, 5.21; N, 6.49%; Requires: C, 56.87; H, 4.77; N, 6.63%.

EXAMPLE 9

Ethyl 2-bromo-3-(3'-methoxyphenyl)-4-fluoro-2-butenoate

Piperidine (0.22 ml) is added to a solution of ethyl 2,3-dibromo-3-(3'-methoxyphenyl)-4-fluorobutyrate (0.80 g) in ether (10 ml). The reaction mixture is stirred at room temperature for 3 hours and water is added. Ether extraction gives essentially pure ethyl 2-bromo-3-(3'-methoxyphenyl)-4-fluoro-2-butenoate (0.65 g).

EXAMPLE 10

2-Amino-3-(3'-hydroxy-4'-methoxyphenyl)-4-fluoro-3-butenoic acid

Repeating the procedures described in Examples 2, 3, 9, 5, and 6, α-fluoro-3-tetrahydropyranyloxy-4-methoxyacetophenone can be converted to ethyl 2-tert-butocycarbonylamino-3-(3'-tetrahydropyranyloxy-4-methoxyphenyl)-4-fluoro-3-butenoate. The conversion of this intermediate to the final product is achieved as follows:

A mixture of this product (0.45 g) and lithium hydroxide monohydrate (0.09 g) in water (3 ml) and THF (13 ml) is stirred at room temperature for 2 hours. Dilute aqueous hydrochloric acid is added to adjust the pH to about 4, then the acid is isolated by ether extraction. The crude material is treated overnight with a saturated solution of hydrogen chloride in ether (20 ml). Filtration affords a colorless powder (0.21 g) which is dissolved in ethanol (20 ml) and treated with propylene oxide (0.20 g) at room temperature overnight. Filtration of the precipitate affords 2-amino-3-(3'-hydroxy-4'-methoxyphenyl)-4-fluoro-3-butenoic acid (0.12 g) as a colorless powder, m.p. 214°:

NMR (D$_2$O+DCl): δ 3.87, s, 3H; 5.00, s, 1H; 6.77 to 7.13, m, 3H; 7.25, d (J=80 Hz), 1H.

Analysis for C$_{11}$H$_{12}$FNO$_4$: Found: C, 54.68; H, 5.18; N, 5.74%; Requires: C, 54.77; H, 5.01; N, 5.81%.

EXAMPLE 11

α-Fluoro-3-tetrahydropyranyloxy-4-methoxyacetophenone

A solution of 3-acetoxy-4-methoxyacetophenone (53 g) in chloroform (700 ml) is cooled in an ice bath and treated slowly with a solution of bromine (41 g) in chloroform (100 ml). The solution is then stirred for 90 minutes after which the chloroform is evaporated. The residue is dissolved in ether, washed in water, dried and evaporated. The solid residue is recrystallized from dichloromethane/hexane to afford α-bromo-3-acetoxy-4-methoxyacetophenone (59.51 g) as colorless plates: m.p. 116°-117°.

A portion (57.4 g) of this bromide, mixed with KH$_2$F (46.8 g) in diethylene glycol (500 ml), is allowed to remain at 100° for 8 hours. The mixture is cooled, poured into ice-water, and extracted with ether. The ether soluble material is purified by silica gel chromatography using light petroleum (50%)/diethyl ether (50%) as eluant whereupon α-fluoro-3-hydroxy-4-methoxyacetophenone (22.4 g) is obtained. Recrystallization from dichloromethane/hexane affords colorless plates (20.2 g): m.p. 70°-71°.

The phenol (18.35 g) is treated with dihydropyran (20 ml) and concentrated hydrochloric acid (10 drops) at room temperature for 3½ hours. The solution is poured into 2% aqueous sodium hydroxide (300 ml) and extracted with ether. The ether soluble material is purified by silica gel chromatography (light petroleum (80%)/diethyl ether (20%)), and by recrystallization from dichloromethane/hexane to afford α-fluoro-3-tetrahydropyranyloxy-4-methoxyacetophenone (17.15 g), as colorless needles: m.p. 78°-79°:

NMR (CDCl$_3$): δ 1.57 to 1.93, m, 6H; 3.43 to 4.10, m and 3.87, s, 5H; 5.40, d (J=47 Hz), 2H; 5.40, s (broad), 1H; 6.80 to 7.63, ABC system, 3H Analysis for C$_{14}$H$_{17}$FO$_4$: Found: C, 62.59; H, 6.32%; Requires: C, 62.68; H, 6.39%.

EXAMPLE 12

2-Amino-4-fluoro-3-(3'-hydroxyphenyl)-3-butenoic acid (herein-after referred to as "AFHBA"), and 2-amino-4-fluoro-3-(3'-hydroxy-4-methoxyphenyl)-3-butenoic acid (herein-after referred to as "AFMBA") were tested as follows:

A. In vitro testing

AFHBA was incubated with partially purified hog kidney AADC at 37° for various times up to 2 hours. HPLC analysis determined that at 2 hours the compound (as the DL-mixture) underwent 50% decarboxylation to give the corresponding allylamine: 2-(3'-hydroxy)-phenyl-3-fluoroallylamine. When the experiment was repeated in the presence of 10 μM α-monofluoromethyl-Dopa (MFMD) (an AADC inhibitor), no decarboxylation was observed.

The decarboxylated product is a time-dependent irreversible inhibitor of MAO in vitro: IC$_{50}$ for 2-(3'-hydroxy)phenyl-3-fluoroallylamine, ~10$^{-9}$. AFHBA is an inactive or very weak inhibitor of MAO.

B. Ex vivo testing

Rats were injected with AFHBA (0.5 mg/kg, i.p.) alone or with AFHBA (0.5 mg/kg, i.p.) in combination with MFMD (2.0 mg/kg, i.p.) administered 30 minutes before AFHBA. Animals were killed 18 hours later and MAO activity (5-HT and phenethylamine as substrates) was determined in brain, heart, and liver. In the brain, AFHBA administered alone inhibited neuronal MAO by 72% and non-neuronal MAO by 37%. Pretreatment with MFMD did not essentially reduce the inhibition of neuronal MAO (68%), but it reduced inhibition of non-neuronal MAO to 28%. In the heart, AFHBA inhibited neuronal MAO by 52% and non-neuronal MAO by 44%, but pretreatment with MFMD reduced neuronal inhibition of MAO to 18% and non-neuronal inhibition to 4%. In the liver, MAO inhibition by AFHBA alone was 29% (neuronal) and 38% (non-neuronal), but pretreatment with MFMD totally blocked MAO inhibition.

When the above experiments with AFHBA were repeated using carbidopa (50 mg/kg, i.p.), the AADC inhibitor produced the same protective effect against inhibition of MAO in the heart as MFMD (2.0 mg/kg, i.p.). To demonstrate the activity of AFHBA by oral administration, rats were gavaged with various doses of the compounds and killed 18 hours later. MAO activity was determined in the brain using 5-HT and phenethylamine (PEA) as substrates. The following results were obtained:

| Dose (mg/kg) | % Inhibition of MAO | |
|---|---|---|
| | Neuronal | Non-neuronal |
| 0.5 | 63 | 41 |
| 1.0 | 71 | 64 |
| 2.5 | 95 | 83 |

III. Rats were injected with AFMBA (100 mg/kg, i.p.) and were killed 18 hours later. MAO activity was determined in the brain, heart, and liver using 5-HT and PEA. The following results were obtained:

|  | % Inhibition of MAO | |
|---|---|---|
|  | Neuronal | Non-neuronal |
| Brain | 16 | 40 |
| Heart | 18 | 46 |
| Liver | 2 | 11 |

C. In vivo testing

Rats were injected with AFHBA (0.5 mg/kg, i.p.) alone or with AFHBA (0.5 mg/kg, i.p.) in combination with MFMD (2 mg/kg, i.p.) or carbidopa (50 mg/kg, i.p.) given 30 minutes before the AFHBA. The rats were killed 18 hours later, and dopamine, DOPAC, 5-HT, and 5-HIAA concentrations were determined in the brain. The following results were obtained:

| Treatment | % Change from Control | | | |
|---|---|---|---|---|
|  | Dopamine | DOPAC | 5-HT | 5-HIAA |
| AFHBA | +25 | −76 | +30 | −34 |
| AFHBA + MFMD | +50 | −92 | +92 | −48 |
| AFHBA + carbidopa | +54 | −89 | +92 | −37 |

In a separate experiment, rats were given AFHBA orally at various doses. The rats were killed 18 hours later and dopamine, DOPAC, 5-HT, and 5-HIAA concentrations were determined in the brain. The following results were obtained:

| Dose (mg/kg) | % Change from Control | | | |
|---|---|---|---|---|
|  | Dopamine | DOPAC | 5-HT | 5-HIAA |
| 0.5 | +8 | −55 | +26 | −11 |
| 1.0 | +17 | −72 | +74 | −23 |
| 2.5 | +28 | −79 | +140 | −41 |

EXAMPLE 13

(A) Rats were gavaged daily for 5 days with saline or 2-amino-4-fluoro-3-(3′-hydroxyphenyl)-3-butenoic acid (AFHBA) at dosages of 15.6, 62.5, 250, or 1000 µg/kg or with clorgyline at dosages of 1250 or 5000 µg/kg. On the 6th day, rats were anaesthetized and heart rate and blood pressure responses to tyramine (0.3–50 mg/kg) administered intraduodenally (i.d.) were determined. Additionally, monoamines and MAO activity were determined in various tissues including brain. The results are shown in Table I.

TABLE I

Comparison Between Brain Amine Changes and Degree of Potentiation of Tyramine Following Administration of Monoamineoxidase Inhibitors in Rats

| Dose[a] (µg/kg) | Brain Amine Concentration (ng/g) | | Tyramine Potentiation[b] |
|---|---|---|---|
|  | Noradrenaline | 5-HT |  |
| Treatment: Saline | | | |
| — | 318 ± 12 | 507 ± 18 | — |
| Treatment: AFHBA | | | |
| 15.6 | 347 ± 9 | 530 ± 27 | 1.0[c] |
| 62.5 | 391 ± 12 | 531 ± 32 | 4.0 |
| 250 | 563 ± 23 | 1082 ± 98 | 7.1 |
| 1000 | 650 ± 29 | 1486 ± 67 | 7.7 |
| Treatment: Clorgyline | | | |
| 1250 | 351 ± 11 | 620 ± 34 | 1.0[c] |
| 5000 | 329 ± 19 | 1027 ± 82 | 5.0 |

[a] given daily, p.o., for 5 days.
[b] dose to raise heart rate by 65 beats/min in saline-treated rats / dose to raise heart rate by 65 beats/min in drug-treated rats
[c] some potentiation of tyramine at lowest doses of tyramine administered.

As seen in Table I, subacute treatment with AFHBA or clorgyline produced dose-related increases in brain noradrenaline and 5-HT concentrations and potentiation of the tyramine response. The threshold dose for both effects was between 15.6 µg/kg and 62.5 µg/kg for AFHBA and between 1250 and 5000 µg/kg for clorgyline, respectively.

(B) Rats were gavaged with saline or carbidopa given at dosage of 10 or 100 mg/kg. Thirty minutes later, the rats were gavaged with saline or AFHBA given at a dosage of 62.5 µg/kg. This treatment was repeated daily for 5 days. On the 6th day, the rats were anaesthetized and heart rate and blood pressure responses to tyramine (0.3–50 mg/kg, i.d.) were determined. Additionally, monoamines and MAO activity were determined in various tissues, including brain. The key results are shown in Table II.

TABLE II

Effects of Pretreatment with Carbidopa on the Brain Amine Changes and the Degree of Potentiation of Tyramine Following Administration of AFHBA in Rats

| Dose[a] (µg/kg) | Brain Amine Concentration (ng/g) | | Tyramine Potentiation[b] |
|---|---|---|---|
|  | Noradrenaline | 5-HT |  |
| Treatment: Saline | | | |
| — | 318 ± 12 | 507 ± 18 | — |
| + AFHBA 62.5 | 391 ± 12 | 531 ± 32 | 4.0 |
| Treatment: Carbidopa 10000 | 366 ± 3 | 599 ± 31 | 1.1 |
| + AFHBA 62.5 | 694 ± 24 | 894 ± 25 | 3.1 (2.8)[c] |
| Treatment: Carbidopa 100000 | 271 ± 19 | 443 ± 19 | 2.3 |
| + AFHBA 62.5 | 327 ± 23 | 815 ± 35 | 5.0 (2.2)[c] |

[a] given daily, p.o., for 5 days.
[b] dose to raise heart rate by 65 beats/min in saline-treated rats / dose to raise heart rate by 65 beats/min in drug-treated rats
[c] figures in brackets indicate degree of potentiation over and above that of carbidopa.

As is seen in Table II, a 100 mg/kg dose of carbidopa is not optimum since given alone it potentiated the tyramine response, and given in combination with AFHBA it reduced the effectiveness of AFHBA to raise brain monoamines. At 10 mg/kg, carbidopa given alone had no effect on tyramine response but it significantly enhanced the elevation of brain monoamines when coadministered with AFHBA at 62.5 µg/kg. However, the combination of carbidopa with AFHBA was still associated with a potentiation of the tyramine response, but the potentiation did not exceed that of AFHBA given alone. In quantitative terms, 62.5 µg/kg of AFHBA combined with 10 mg/kg carbidopa produced an effect on brain monoamines at least equivalent to 250 µg/kg of AFHBA given alone or to 5000 µg/kg of clorgyline, while producing the least potentiation of the tyramine response.

What is claimed is:

1. A compound of the formula:

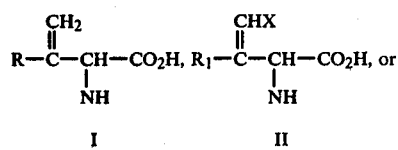

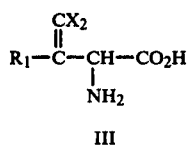

wherein:

X is fluorine, chlorine, or bromine;
R is the group $R_2$ as defined below;
$R_1$ is a group of the formula:

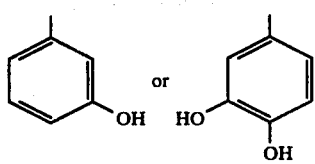

or the group $R_2$ as defined below; wherein $R_2$ is:

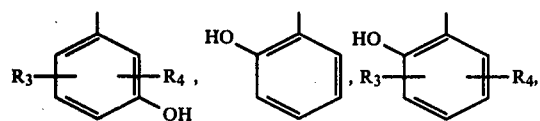

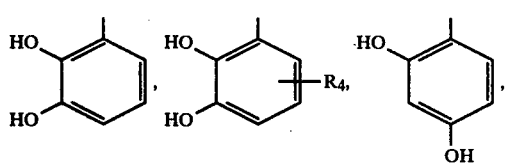

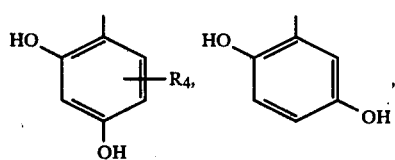

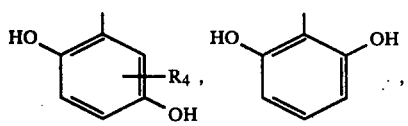

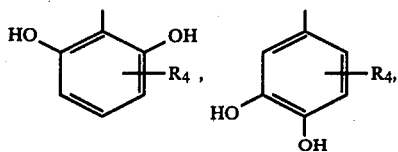

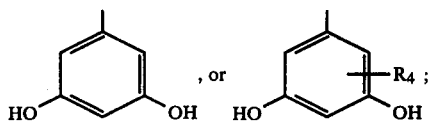

wherein $R_3$ is hydrogen, $(C_1-C_4)$alkyl, or $(C_1-C_4)$alkoxy, and $R_4$ is $(C_1-C_4)$alkyl or $(C_1-C_4)$alkoxy; or a $(C_1-C_8)$alkyl ester thereof; or a non-toxic pharmaceutically acceptable salt thereof.

2. A compound of Formula I as defined in claim 1.
3. A compound of Formula II as defined in claim 1.
4. A compound of Formula III as defined in claim 1.
5. A compound as defined in claim 2, 3, or 4 wherein X is fluorine.
6. A compound as defined in claim 3 or 4 wherein $R_1$ is:

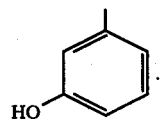

7. A compound as defined in claim 6 wherein X is fluorine.
8. A compound as defined in claim 7 which is 2-amino-4-fluoro-3-(3′-hydroxyphenyl)-3-butenoic acid or a non-toxic pharmaceutically acceptable salt thereof.
9. A compound as defined in claim 7 which is 2-amino-4-fluoro-3-(3′-hydroxyphenyl)-3-butenoic acid, $(C_1-C_8)$alkyl ester or a non-toxic pharmaceutically acceptable acid addition salt thereof.
10. A compound as defined in claim 9 which is 2-amino-4-fluoro-3-(3′-hydroxyphenyl)-3-butenoic acid, methyl ester or a non-toxic pharmaceutically acceptable acid addition salt thereof.
11. A compound as defined in claim 9 which is 2-amino-4-fluoro-3-(3′-hydroxyphenyl)-3-butenoic acid, ethyl ester or a non-toxic pharmaceutically acceptable acid addition salt thereof.
12. A compound as defined in claim 2, 3, or 4 wherein R or $R_1$ is:

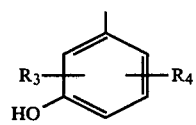

wherein $R_3$ is hydrogen, $(C_1-C_4)$alkyl, or $(C_1-C_4)$alkoxy, and $R_4$ is $(C_1-C_4)$alkyl or $(C_1-C_4)$alkoxy.

13. A compound as defined in claim 12 wherein $R_3$ is hydrogen.
14. A compound as defined in claim 12 wherein X is fluorine.
15. A compound as defined in claim 13 wherein X is fluorine.

16. A pharmaceutical composition comprising (a) a compound as defined in claim 1, and (b) a pharmaceutically acceptable carrier or diluent.

17. A pharmaceutical composition as defined in claim 16 in unit dosage form containing 10 μg to 100 mg of said compound per unit dose.

18. A pharmaceutical composition comprising (a) a compound as defined in claim 1, (b) an aromatic L-amino acid decarboxylase (AADC) inhibitor, and (c) a pharmaceutically acceptable carrier or diluent.

19. A pharmaceutical composition as defined in claim 18 wherein the AADC inhibitor is carbidopa, benzerazide, or a 2-amino-2-(monofluoromethyl or difluoromethyl)-3-(monohydroxyphenyl or dihydroxyphenyl)propionic acid.

20. A composition as defined in claim 19 wherein the AADC inhibitor is carbidopa.

21. A composition as defined in claim 16, 17, 18, 19, or 20 wherein said compound is 2-amino-4-fluoro-3-(3'-hydroxyphenyl)-3-butenoic acid or a non-toxic pharmaceutically acceptable salt thereof.

22. A composition as defined in claim 16, 17, 18, 19, or 20 wherein said compound is 2-amino-4-fluoro-3-(3'-hydroxyphenyl)-3-butenoic acid, (C$_1$–C$_8$)alkyl ester or a non-toxic pharmaceutically acceptable acid addition salt thereof.

23. A composition as defined in claim 22 wherein said compound is 2-amino-4-fluoro-3-(3'-hydroxyphenyl)-3-butenoic acid, methyl ester or a non-toxic pharmaceutically acceptable acid addition salt thereof.

24. A composition as defined in claim 22 wherein said compound is 2-amino-4-fluoro-3-(3'-hydroxyphenyl)-3-butenoic acid, ethyl ester or a non-toxic pharmaceutically acceptable acid addition salt thereof.

25. A composition as defined in claim 16, 17, 18, 19, or 20 wherein said compound is a compound of Formula II as defined in claim 1, wherein R$_1$ is:

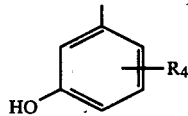

wherein R$_4$ is (C$_1$–C$_4$)alkyl or (C$_1$–C$_4$)alkoxy.

26. A composition as defined in claim 25 wherein X is fluorine.

27. A method for treating depression which comprises administering to a depressed patient an effective amount of a compound as defined in claim 1.

28. A method for treating depression which comprises administering to a depressed patient on effective amount of a compound as defined in claim 1 in combination with an effective amount of an aromatic L-amino acid decarboxylase (AADC) inhibitor, the amount of inhibitor being sufficient to substantially block the AADC catalyzed decarboxylation of said compound extracerebrally without substantially blocking the AADC catalyzed decarboxylation of said compound in the brain.

29. A method as defined in claim 28 wherein the AADC inhibitor is carbidopa, benzerazide, or a 2-amino-2-(monofluoromethyl or difluoromethyl)-3-(monohydroxyphenyl or dihydroxyphenyl)propionic acid.

30. A method as defined in claim 29 wherein the AADC inhibitor is carbidopa.

31. A method as defined in claim 27, 28, 29, or 30 wherein said compound administered is 2-amino-4-fluoro-3-(3'-hydroxyphenyl)-3-butenoic acid or a non-toxic pharmaceutically acceptable salt thereof.

32. A method as defined in claim 27, 28, 29, or 30 wherein said compound administered is 2-amino-4-fluoro-3-(3'-hydroxyphenyl)-3-butenoic acid, (C$_1$–C$_8$)alkyl ester or a non-toxic pharmaceutically acceptable acid addition salt thereof.

33. A method as defined in claim 32 wherein said compound administered is 2-amino-4-fluoro-3-(3'-hydroxyphenyl)-3-butenoic acid, methyl ester or a non-toxic pharmaceutically acceptable acid addition salt thereof.

34. A method as defined in claim 32 wherein said compound administered is 2-amino-4-fluoro-3-(3'-hydroxyphenyl)-3-butenoic acid, ethyl ester or a non-toxic pharmaceutically acceptable acid addition salt thereof.

35. A method as defined in claim 27, 28, 29, or 30 wherein said compound administered is a compound of Formula II as defined in claim 1 wherein R$_1$ is:

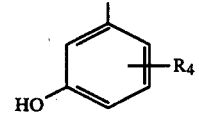

wherein R$_4$ is (C$_1$–C$_4$)alkyl or (C$_1$–C$_4$)alkoxy.

36. A method as defined in claim 35 wherein X is fluorine.

* * * * *